United States Patent [19]

Crowell et al.

[11] Patent Number: 6,147,115

[45] Date of Patent: Nov. 14, 2000

[54] ANTITUMOR COMPOSITIONS AND METHODS OF TREATMENT

[75] Inventors: Thomas A. Crowell; J. Jeffry Howbert; John S. Ward, all of Indianapolis, Ind.

[73] Assignee: Eli Lilly and Company, Indianapolis, Ind.

[21] Appl. No.: 08/036,640

[22] Filed: Mar. 24, 1993

Related U.S. Application Data

[62] Division of application No. 07/554,218, Jul. 17, 1990, Pat. No. 5,216,026.

[51] Int. Cl.⁷ .................. A61K 31/175; C07C 311/54
[52] U.S. Cl. .................................. 514/592; 564/39
[58] Field of Search ..................... 564/39; 514/592

[56] References Cited

U.S. PATENT DOCUMENTS

| | | | |
|---|---|---|---|
| 2,979,437 | 4/1961 | McLamore et al. | 514/592 |
| 2,990,326 | 6/1961 | Aumuller et al. | 514/592 |
| 3,083,207 | 3/1963 | Hoehn et al. | 514/592 |
| 3,097,240 | 7/1963 | Aumuller et al. | 514/592 |
| 3,097,241 | 7/1963 | Korger et al. | 514/592 |
| 3,097,242 | 7/1963 | Hoehn et al. | 514/592 |
| 3,102,115 | 8/1963 | Breuer et al. | 514/592 |
| 3,102,121 | 8/1963 | Breuer et al. | 514/592 |
| 3,155,721 | 11/1964 | Mills et al. | 514/592 |
| 3,320,312 | 5/1967 | Sigal et al. | 514/592 |
| 3,418,367 | 12/1968 | Dietrich | 514/592 |
| 3,849,110 | 11/1974 | Soper et al. | 514/592 |
| 3,983,107 | 9/1976 | Holland | 514/592 |
| 4,045,209 | 8/1977 | Hainaut et al. | 514/592 |
| 4,276,290 | 6/1981 | Weir et al. | 514/592 |
| 4,725,679 | 2/1988 | Willms | 514/592 |
| 4,845,128 | 7/1989 | Harper et al. | 514/592 |

FOREIGN PATENT DOCUMENTS

| | | |
|---|---|---|
| 0228642 | 5/1959 | Australia ............... 564/39 |
| 0601648 | 7/1960 | Canada ................. 564/39 |
| 1208561 | 7/1986 | Canada . |
| 0093622 | 6/1958 | Denmark . |
| 107214 | 9/1983 | European Pat. Off. . |
| 123303 | 4/1984 | European Pat. Off. . |
| 166615 | 1/1986 | European Pat. Off. . |
| 222475 | 9/1986 | European Pat. Off. . |
| 291269 | 5/1988 | European Pat. Off. . |
| 1240866 | 6/1961 | Germany . |
| 1144259 | 2/1963 | Germany . |
| 1159937 | 12/1963 | Germany . |

OTHER PUBLICATIONS

Ruschig et al. in *Arzneimeit–Forsch.* 8, 448 (1958).
Chemical Abstracts, vol. 54, 5532d (1960) cites an article by Palazzo et al. *Farmaco. Ed. Sci.*, 14, 358–62 (1959).
*Chemical Abstracts*, vol. 52, 17180i citing Haack et al., Ger. (East) 9688, Apr. 21, 1955.
Giorgetti in *Bulletin De La Societe Chimique De France*, 1971, No. 10, pp. 3600.
Hartig in the *Journal fur Praktische Chemie*, vol. 305, Series 4, pp. 215 (1966).
Cassady et al., *J. Org. Chem.*, 23, 923 (1958).
S. Petersen, *Chem. Ber.*, 83, 551 (1950).
Houghton et al. in *Cancer Chemother Pharmacol* (1989), 25:84–88.
Grindey et al., *Proceedings of the American Association for Cancer Research*, 27, Mar. 1986 (Abstract 1099).
Grindey et al., *Proceedings of the American Association for Cancer Research*, 28, 309 (1987) (Abstract No. 1224).
*Diabetes*, 19, iii–v(1970).
T. P. Gandhi, et al., *Arzneim.–Forsch.*, 21, 961 (1971).
Gandhi et al., *Arzneim. –Forsch.*, 21, 968 (1971).
Hasegawa et al., *Chemical Society of Japan*, vol. 51, 1805 (1978).
F. Kurzer, *Chem. Rev.*, 50, 1 (1952).
Marshall et al., *J. Org. Chem.*, 23, 927 (1958).
Marshall et al., *J. Med. Chem.*, 6, 60 (1963).
Shah et al., *J. Med. Chem.*, 12, 938 (1969).
Breuer et al., *Chimie Therapeutique*, 659 (1973).
Lerner et al., *Metabolism*, 14, 578 (1965).
Holland et al., *J. Med. Pharm. Chem.*, 3, (1), 99 (1961).
Chemical Abstract vol. 56, 7185a citing Kessler et al., *J. Pharm. Sci.*, 50, 842–4 (1961).

*Primary Examiner*—Shailendra Kumar
*Attorney, Agent, or Firm*—Robert D. Titus; Paul J. Gaylo

[57] ABSTRACT

This invention provides certain sulfonamide compounds, formulations, and a method for treating susceptible neoplasms in mammals using certain sulfonamide compounds.

9 Claims, No Drawings

ANTITUMOR COMPOSITIONS AND METHODS OF TREATMENT

This application is a division, of application Ser. No. 07/554,218 filed Jul. 17, 1990, now U.S. Pat. No. 5,216,026.

BACKGROUND OF THE INVENTION

According to the American Cancer Society about 494,000 people died from cancer in the United States in 1988. One of every five deaths from all causes in the United States is from cancer. Although chemotherapy has become one of the principal methods of treating cancer, the rate at which new drugs have become available for use in cancer chemotherapy has declined in recent years as reported by Horowitz et al. "Phase II Testing of Melphalan in Children with Newly Diagnosed Rhabdomyosarcoma: A Model for Anticancer Drug Development", *Journal of Clinical Oncology*, Vol. 6, No. 2, pp. 308–314 (1988). Accordingly, there is a substantial need for new drugs which are effective in inhibiting the growth of tumors.

To be particularly useful, a new chemotherapeutic agent should have a wide spectrum of activity, a large therapeutic index, and be chemically stable and compatible with other agents. Additionally, it would be beneficial for the new agent to have oral activity so that initial treatment and subsequent maintenance therapy is more convenient and less traumatic to the patient.

It has now been found that certain N-phenyl-N'-alkylsulfonylureas are particularly useful in the treatment of solid tumors. These compounds are relatively nontoxic and provide an excellent therapeutic index.

Some N,N'-diarylsulfonylureas have been reported as being active antitumor agents e.g., U.S. Pat. No. 4,845,128 of Harper et al. (1989) and Grindey et al. *American Association of Cancer Research*, Vol. 27, pp. 277 (1986). There is no suggestion in these references of the N-phenyl-N'-sulfonylureas of the instant application or that these compounds would be useful as antitumor agents.

Certain arylalkylsulfonylureas have been reported in the literature. U.S. Pat. No. 2,979,437 of McLamore et al. (1961) discloses compounds of the general formula RCH=CHSO$_2$NHCONHR' in which R can be a phenyl or substituted phenyl and R' can be p-chloro- or p-bromophenyl as having hypoglycemic activity. *Chemical Abstracts*, Vo. 54, 5532d (1960) cites an article by Palazzo et al. (*Farmaco. Ed. Sci.*, 14, 358–62 (1959)) which discloses N-(p-chlorophenyl)-N'-butylsulfonylurea. The compound is disclosed as producing hypoglycemia in rabbits after oral administration.

Giorgetti in *Bulletin De La Societe Chimique. De France*, 1971, No. 10, pp. 3600 discloses the preparation of a sulfonylurea with formula CH$_2$=CHSO$_2$NHCONHR where R is 3,4-dichlorophenyl.

Holland in U.S. Pat. No. 3,983,107 (1976) also discloses certain 2-phenylethenesulfonamide derivatives of the general formula RCH=CHSO$_2$NHCONR$^1$R$^2$ where R is a phenyl and R$^1$ and R$^2$ can be hydrogen or a substituted phenyl. These compounds are disclosed as being useful for reducing elevated serum lipid levels in mammals.

Hainaut et al. in U.S. Pat. No. 4,045,209 (1977) disclose compounds of the formula XSO$_2$(CH$_2$)$_n$NCH$_3$—CONYR where n is 0 or 1, X can be a C$_1$–C$_6$ alkyl, Y can be hydrogen and R is a phenyl group which can be substituted with hydrogen, chlorine or bromine. These compounds having a methyl substituent on the nitrogen adjacent to the sulfonyl group are disclosed as being useful as herbicides.

None of these references suggest or disclose the antitumor activity of the sulfonylurea compounds of the instant invention. Additionally, there is no suggestion or disclosure of the claimed compounds of the instant invention.

SUMMARY OF THE INVENTION

A method is provided for treating susceptible neoplasms in mammals which comprises administering to a mammal in need of such treatment an effective amount of a compound of the Formula I

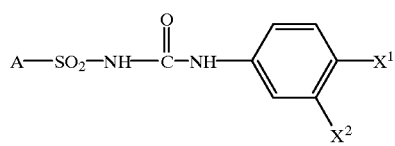

wherein

X$^1$ is halo;

X$^2$ is hydrogen, halo, or CF$_3$;

A is: C$_2$–C$_7$ alkyl; C$_2$–C$_7$ alkenyl; C$_4$–C$_8$ cycloalkyl; phenyl-substituted C$_1$–C$_4$ alkyl; phenyl-substituted C$_2$–C$_4$ alkenyl; or RZR$^1$ where R is phenyl, or C$_1$–C$_3$ alkyl, R$^1$ is (CH$_2$)$_n$ where n is 1–3, and Z is oxygen or sulfur;

and pharmaceutically acceptable salts thereof.

In a further embodiment the instant invention comprises compounds of the Formula II

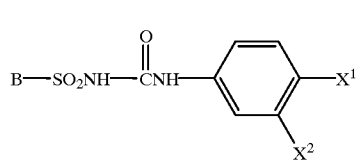

wherein

X$^1$ and X$^2$ are as defined hereinabove;

B is: C$_2$–C$_7$ alkyl with the proviso that when B is n-butyl then X$^1$ is bromo or X$^2$ is other than hydrogen; C$_3$–C$_7$ alkenyl; phenyl-substituted C$_1$–C$_4$ alkyl; phenyl-substituted C$_2$–C$_4$ alkenyl with the proviso that when the alkenyl is C$_2$ and X$^1$ is chloro then X$^2$ is not hydrogen or chloro and when X$^1$ is bromo then X$^2$ is not hydrogen; C$_4$–C$_8$ cycloalkyl; or RZR$^1$—where R is phenyl or C$_1$–C$_3$ alkyl, R$^1$ is (CH$_2$)$_n$ where n is 1–3, and Z is oxygen or sulfur; and pharmaceutically acceptable salts thereof.

In a further embodiment this invention provides pharmaceutical formulations comprising a compound of Formula II in combination with a suitable pharmaceutical excipient. These formulations are particularly useful in treating mammals suffering from susceptible neoplasms.

In another embodiment this invention involves a method for treating susceptible neoplasms in mammals by administering to the mammal an effective amount of a pharmaceutical formulation which comprises a compound of Formula I in combination with a suitable excipient.

DETAILED DESCRIPTION

As used herein the term "halo" refers to fluoro, chloro, bromo and iodo. The term "C$_2$–C$_7$ alkyl" refers to straight and branched chain alkyl groups including ethyl, n-propyl, isopropyl, n-butyl, isobutyl, s-butyl, n-pentyl, isopentyl, 2-methylbutyl, n-hexyl, 2-methylpentyl, and the like. The term "alkenyl" refers to unsaturated alkyl groups with the term "$C_2$–$C_7$ alkenyl" referring to vinyl, 1-propenyl, 1-methylvinyl, 1-butenyl, 1-methyl-1-propenyl, 1-hexenyl, and the like. The term "$C_4$–$C_8$ cycloalkyl" refers to cyclic alkyl groups such as cyclobutyl, cyclopentyl, cyclohexyl, and lower alkyl substituted cyclopentyl and cyclohexyl groups such as methylcyclopentyl, etc. The term "phenyl-substituted $C_1$–$C_4$ alkyl" refers to $C_1$–$C_4$ alkyl groups which are substituted with phenyl groups such as phenylmethyl, phenylethyl and the like. The term "phenyl-substituted alkenyl" refers to phenyl-substituted lower alkenyl groups such as $C_6H_5CH=CH-$ (i.e., styryl) $C_6H_5CH_2CH=CH-$, and the like. The term "alkylsulfonylurea" is used herein to generically encompass all of the foregoing substituents on the sulfonyl group.

The compounds of Formula I and Formula II can be referred to as derivatives of N-[[(substituted phenyl)amino]carbonyl]alkylsulfonamides. Alternatively the compounds can be referred to as 1- and 3-substituted sulfonylureas or N- and N'-substituted sulfonylureas.

Preferred compounds of the instant method are those in Formula I in which $X^1$ is chloro, bromo or fluoro, $X^2$ is hydrogen or chloro and A is $C_3$–$C_6$ alkyl, $C_5$–$C_6$ cycloalkyl, $C_4$–$C_6$ alkenyl, styryl, phenylthiomethyl, or ethoxyethyl.

More preferred compounds of Formula I include: N-[[(3-chloro-4-fluorophenyl)amino]carbonyl]-2-propanesulfonamide; N-[[(4-chlorophenyl)amino]carbonyl]-2-methyl-1-propanesulfonamide; N-[[(4-fluorophenyl)amino]carbonyl]cyclopentanesulfonamide; N-[[(4-fluorophenyl)amino]carbonyl]-2-butanesulfonamide; N-[[(3,4-dichlorophenyl)amino]carbonyl]-2-propanesulfonamide; N-[[(4-chlorophenyl)amino]carbonyl]-2-propanesulfonamide; N-[[(4-bromophenyl)amino]carbonyl]-2-propanesulfonamide; N-[[(3-trifluoromethyl-4-chlorophenyl)amino]carbonyl]-2-propanesulfonamide; N-[[(4-chlorophenyl)amino]carbonyl]-cyclohexanesulfonamide; N-[[(4-bromophenyl)amino]carbonyl]cyclopentanesulfonamide; N-[[(4-chlorophenyl)amino]carbonyl]-2-ethoxyethanesulfonamide; N-[[(3,4-dichlorophenyl)amino]carbonyl]-2-butanesulfonamide; and N-[[(4-chlorophenyl)amino]carbonyl]-2-butene-2-sulfonamide.

Most preferred compounds of the instant method include: N-[[(4-chlorophenyl)amino]carbonyl]-2-butanesulfonamide; N-[[(4-chlorophenyl)amino]carbonyl]-1-butanesulfonamide; N-[[(4-chlorophenyl)amino]carbonyl]-cyclopentanesulfonamide; N-[[(4-chlorophenyl)amino]-carbonyl]-2-phenylethenesulfonamide; N-[[(4-chlorophenyl)amino]carbonyl]phenylmethanesulfonamide; N-[[(4-chlorophenyl)amino]carbonyl]phenylthiomethanesulfonamide; N-[[(4-chlorophenyl)amino]carbonyl]-1-butene-1-sulfonamide; N-[[(4-chlorophenyl)amino]carbonyl]-1-pentanesulfonamide; and N-[[(4-chlorophenyl)amino]carbonyl]-1-hexanesulfonamide.

Preferred compounds of Formula II include those in which: $X^1$ is chloro, bromo or fluoro; $X^2$ is hydrogen, chloro, or trifluoromethyl; B is: (a) $C_3$–$C_6$ alkyl with the proviso that when the alkyl is n-butyl then $X^1$ is bromo or $X^2$ is not hydrogen; (b) $C_4$–$C_5$ alkenyl; (c) phenyl-substituted $C_1$–$C_2$ alkyl; (d) phenyl-substituted $C_2$–$C_3$ alkenyl with the proviso that when the alkenyl group is $C_2$ and $X^1$ is chloro then $X^2$ is not hydrogen of chloro and when $X^1$ is bromo then $X^2$ is not hydrogen; (e) $C_5$–$C_6$ cycloalkyl; or (f) $RZR^1$— where R is phenyl or $C_1$–$C_2$ alkyl, $R^1$ is $CH_2$ or $C_2H_4$, and Z is O or S; and pharmaceutically acceptable salts thereof.

More preferred compounds of Formula II include: N-[[(3-chloro-4-fluorophenyl)amino]carbonyl]-2-propanesulfonamide; N-[[(4-fluorophenyl)amino]carbonyl]-2-butanesulfonamide; N-[[(3,4-dichlorophenyl)amino]carbonyl]-2-propanesulfonamide; N-[[(4-chlorophenyl)amino]carbonyl]-2-propanesulfonamide; N-[[(4-bromophenyl)amino]carbonyl]-2-propanesulfonamide; N-[[(3-trifluoromethyl-4-chlorophenyl)amino]carbonyl]-2-propanesulfonamide; N-[[(4-chlorophenyl)amino]carbonyl]-cyclohexanesulfonamide; N-[[(4-bromophenyl)amino]carbonyl]cyclopentanesulfonamide; N-[[(4-chlorophenyl)amino]carbonyl]-2-ethoxyethanesulfonamide; N-[[(3,4-dichlorophenyl)amino]carbonyl]-2-butanesulfonamide; N-[[(4-chlorophenyl)amino]carbonyl]-2-butene-2-sulfonamide; N-[[(4-chlorophenyl)amino]carbonyl]-2-butanesulfonamide; N-[[(4-chlorophenyl)amino]-carbonyl]cyclopentanesulfonamide; N-[[(4-chlorophenyl)amino]carbonyl]phenylmethanesulfonamide; N-[[(4-chlorophenyl)amino]carbonyl]phenylthiomethanesulfonamide; N-[[(4-chlorophenyl)amino]carbonyl]-1-butene-1-sulfonamide; N-[[(4-chlorophenyl)amino]carbonyl]-2-methyl-1-propanesulfonamide; N-[[(4-fluorophenyl)amino]carbonyl]cyclopentanesulfonamide; N-[[(4-chlorophenyl)amino]carbonyl]-1-pentanesulfonamide; and N-[[(4-chlorophenyl)amino]carbonyl]-1-hexanesulfonamide.

This invention includes the pharmaceutically acceptable salts of the compounds of Formula I and Formula II. The compounds of this invention can be contacted with basic materials such as alkali metal- or alkaline earth metal hydroxides, carbonates, and bicarbonates, including sodium hydroxide, potassium hydroxide, lithium hydroxide, calcium hydroxide, sodium bicarbonate, etc., to form the corresponding metal salt such as the sodium, potassium, lithium or calcium salt. Nontoxic organic bases can also be used including primary, secondary and tertiary alkyl amines such as methylamine, triethylamine, and the like.

The compounds of Formula I and Formula II can be prepared by any of the methods known in the literature. Generally these methods involve either the reaction of a sulfonamide with an isocyanate or a reaction of a sulfonyl-carbamate with an amine. A preferred method of preparing the instant compounds involves the reaction of a sulfonamide of Formula IIIa

A—$SO_2NH_2$ or B—$SO_2NH_2$     IIIa with a basic material to provide the reactive anion of Formula III$_b$

A—or B—$SO_2NH^-$, M+     IIIb wherein M+ is a counter ion, prior to contacting an arylisocyanate of Formula IV

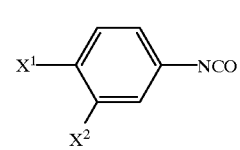

IV where A, B, $X^1$, and $X^2$ are the same as previously defined.

A basic material such as sodium hydroxide, potassium hydroxide, lithium hydroxide, sodium methoxide, sodium hydride and the like can be contacted with the sulfonamide and the resulting product $III_b$ then contacted with the isocyanate. The reaction between anion $III_b$ and isocyanate IV is usually performed using equal molar amounts of the two reactants although other ratios are operative. The reaction is preferably carried out in a solvent which is nonreactive under the reaction condition such as benzene, toluene, acetonitrile, ethyl ether, dioxane, or most preferably acetone or tetrahydrofuran. The reaction can be carried out at temperatures from about 0° C. normally up to the boiling point of the reaction mixture. At the preferred temperature range of about 0° to 50° C., the reaction is usually complete within two hours. The resulting product is preferably neutralized with an acid such as hydrochloric acid and recovered by filtration. If desired, the product can be purified by any number of methods known to those skilled in the art such as chromatography or crystallization.

The sulfonamide of Formula $III_a$ can be prepared by one of several methods. Generally, the sulfonamides can be prepared by ammonolysis of the appropriate sulfonyl chloride:

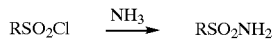

This preparation can be performed using ammonia, with or without a cosolvent such as tetrahydrofuran, or using aqueous ammonia, with or without a cosolvent such as tetrahydrofuran, dichloromethane, etc. Arylthiomethane sulfonamides can be prepared using the method disclosed in *J. Chem. Engineering Data*, 21, 237 (1976). Alkenylsulfonamides can be prepared according to the method disclosed in *J. Org. Chem.*, 49, 1700 (1984). These articles are incorporated herein by reference in their entirety.

Styrene sulfonyl chlorides can be prepared using the method of Culbertson and Dietz, *J. Chem. Soc.* [C], 992 (1968) with dimethylformamide (DMF) and sulfonyl chloride as follow:

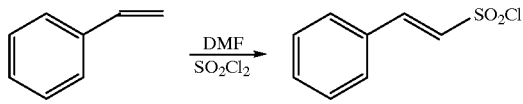

Benzyl and alkyl sulfonyl chlorides can be prepared by chlorination of isothiouronium salts, which are derived from the corresponding benzyl or alkyl halides:

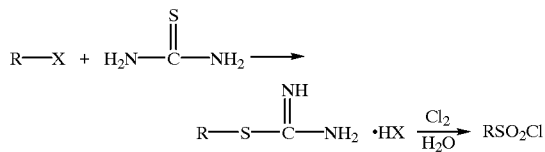

where X is Cl, Br, or I.

Chlorination of other thio-containing compounds can also be used. This procedure as well as other general preparations of sulfonyl halides are disclosed in *Advanced Organic Chemistry*, 3rd Ed., Jerry March, John Wiley & Sons (1985), indexed on page 1172 and all are incorporated herein by reference.

The starting materials and intermediates for these preparations are commercially available or can be readily prepared by the above-described methods or other methods known in the literature.

The terms and abbreviations used in the instant examples have their normal meaning unless otherwise designed, for example, "THF" means tetrahydrofuran; "° C." refers to degrees celsius; "N" refers to normal or normality; "mmole" refers to millimole; "g" refers to gram; "ml" means milliliter; "M" refers to molar; "NMR" refers to proton nuclear magnetic resonance; and "m.s." refers to mass spectrometry.

The following examples further illustrate the preparation of the compounds of this invention. The examples are provided for purposes of illustration only and are not to be construed as limiting the scope of the instant invention in any way.

EXPERIMENTAL

Procedure A

The sulfonamide was dissolved in acetone. An aqueous solution of 1.0N sodium hydroxide was added at room temperature. Additional water and acetone was added as necessary to dissolve any solid formed. An acetone solution of the isocyanate was added. The mixture was stirred, and the solvent was removed to provide a residue. Water was added to the residue, the mixture was acidified, and the solid product was collected.

Procedure B

Same as Procedure A except the sulfonamide was dissolved in methanol and a solution of sodium methoxide in methanol was used instead of sodium hydroxide. The methanol was removed and tetrahydrofuran (THF) was added to the residue. The isocyanate was added to the mixture and stirred. After removing the tetrahydrofuran the residue was dissolved in water, filtered, and the water removed to provide the sodium salt of the product.

EXAMPLE 1

Preparation of N-(4-chlorophenyl)-N'-1-propanesulfonylurea

Procedure A was followed with 1-propanesulfonamide (5.0 g, 40.6 mmole), in acetone (40 ml), and 1.0N sodium hydroxide (40.6 ml). After ten minutes of stirring, 4-chlorophenyl isocyanate (6.2 g, 40.6 mmole) dissolved in about 40 ml of acetone was added over a five minute period. The mixture was allowed to stir for about two hours and filtered. The filtered solid was washed with water which dissolved most of it. 1N HCl (40 ml) was added to the combined filtrates and the resulting precipitate was filtered off and dried at about 65° C. under vacuum to provide 7.2 g of product.

NMR: 300 MHz DMSO 1.01 (t, J=8 Hz, 3H), 1.74 (sextet, J=8 Hz, 2H), 3.42 (t, J=8 Hz, 2H), 7.42 (ABq, J=9 Hz, Δv=27 Hz, 4H), 8.96 (s, 1H), 10.30 (v br s, 1H); MS: 276 (M+); Analysis for $C_{10}H_{13}N_2SO_3Cl$: Theory: C, 43.40; H, 4.74; N, 10.12; S, 11.59; Found: C, 43.19 H, 4.77; N, 10.24; S, 11.66.

EXAMPLE 2

Preparation of N-(4-fluorophenyl)-N'-2-propanesulfonylurea sodium salt

The procedure of Example B was followed with 2-propanesulfonamide sodium salt (4.35 g, 30 mmole) in THF (200 ml) and 4-fluorophenyl isocyanate (4.11 g) in THF (50 ml). The residue was crystallized from isopropanol to provide product which was dried at 70° for two days. The solid did not have a sharp melting point but decomposed above 160° C.

NMR: 60 MHZ DMSO 1.17 (d, J=7 Hz, 6H), 3.25 (m, 1H), 6.93 (t, J=9 Hz, 2H), 7.52 (dd, J=6, 9 Hz, 2H), 8.35 (br s, 1H); Analysis for $C_{10}H_{12}FN_2O_3S.Na$: Theory: C, 42.55; H, 4.29; N, 9.92; Found: C, 42.55; H, 4.33; N, 9.65.

EXAMPLE 3

Preparation of N-(4-chlorophenyl)-N'-2-propanesulfonylurea sodium salt

Procedure B was followed using 2-propanesulfonamide sodium salt (17.4 g) in THF (500 ml) and 4-chlorophenyl isocyanate (18.7 g). After stirring the mixture overnight, the resulting solid was removed by filtration, dried under vacuum at 60° C. following by drying under vacuum at 100° C. overnight to provide 31 g of product. Melting point 257–258° C.

NMR: 60 MHz DMSO 1.18 (d, J=7 Hz, 6H), 3.25 (m, 1H), 7.33 (ABq, J=9 Hz, Δv=26 Hz, 4H), 8.47 (br s, 1H); Analysis for $C_{10}H_{12}N_2O_3SCl.Na$: Theory: C, 40.21; H, 4.05; N, 9.38; Found: C, 40.47; H, 3.93; N, 9.21.

EXAMPLE 4

Preparation of N-(4-bromophenyl)-N'-2-propanesulfonylurea sodium salt

Procedure B was followed using 2-propanesulfonamide sodium salt (4.35 g) in THF (200 ml), 4-bromophenyl isocyanate (5.94 g) in THF (100 ml) and dimethylformamide (25 ml). After stirring overnight, a solid was separated by filtration, dissolved in isopropyl alcohol/water and recrystallized to provide 7.1 g of product which after drying two days at 70° C. did not have a sharp melting point and decomposed above 140° C.

NMR: 60 MHz DMSO 1.22 (d, J=7 Hz, 6H), 3.30 (m, 1H), 7.43 (ABq, J=9 Hz, Δv=17 Hz, 4H), 8.58 (br s, 1H); Analysis for $C_{10}H_{12}N_2O_3SBr.Na$: Theory: C, 35.00; H, 3.52; N, 8.16; Found: C, 35.17; H, 3.73; N, 8.15.

EXAMPLE 5

Preparation of N-(3,4-difluorophenyl)-N'-2-propanesulfonylurea sodium salt

N-(2-butanesulfonyl)carbamate sodium salt (4.9 g) was combined with dry toluene (200 ml), and trimethylsilyl chloride (3 ml) and 3,4-difluoroaniline (2.6 g) were added to the mixture. The reaction mixture was heated to reflux and stirred overnight. The reaction mixture was cooled to below room temperature. The resulting solid was removed by filtration, washed with water, and dried to give 4.5 g of solid product. The solid was dissolved in 1 equivalent aqueous NaOH and the water evaporated to provide the Na salt. Crystallization from isopropyl alcohol provided 4.0 g of solid product. Melting point 205–7° C.

NMR: 60 MHz DMSO 1.17 (d, J=7 Hz, 6H), 3.25 (m, 1H), 6.95–8.10 (m, 3H), 8.60 (br s, 1H); Analysis for $C_{10}H_{11}N_2O_3SF_2.Na$: Theory: C, 40.00; H, 3.69; N, 9.33; Found: C, 40.18; H, 3.73; N, 9.12.

EXAMPLE 6

Preparation of N-(3-chloro-4-fluorophenyl)-N'-2-propanesulfonylurea sodium salt

Procedure B was followed using 2-propanesulfonamide sodium salt (4.35 g) in THF (150 ml) and 3-chloro-4-fluorophenyl isocyanate (5.14 g) in THF (50 ml). The mixture was stirred overnight. The recovered solid was crystallized from isopropyl alcohol and dried at 70° C. under vacumm overnight.

NMR: 60 MHz DMSO 1.17 (d, J=7 Hz, 6H), 3.30 (m, 1H), 6.97–7.50 (m, 2H), 7.93 (dd, J=2,7 Hz, 1H), 8.57 (br s, 1H); Analysis for $C_{10}H_{11}N_2O_3SFCl.Na$: Theory: C, 37.92; H, 3.50; N, 8.85; Found: C, 37.95; H, 3.68; N, 8.79.

EXAMPLE 7

Preparation of N-(3,4-dichlorophenyl)-N'-2-propanesulfonylurea 2-propanesulfonamide (4.40 g) was combined with THF (150 ml) and then dimethylformamide (40 ml) and sodium hydride (2.1 g) were added and the mixture stirred two hours at room temperature. To the mixture was added 3,4-dichlorophenyl isocyanate (7.52 g) in THF (50 ml) and the mixture stirred overnight. The solvent was removed under vacuum, water was added and the mixture filtered. The filtrate was evaporated and then more water introduced when crystals did not form. The solution was made acidic and stirred overnight. The precipitated solid was recovered by filtration. Recrystallization from toluene provided 4.9 g of product with a melting point 151–4° C.

NMR: 60 MHz DMSO 1.32 (d, J=7 Hz, 6H), 3.72 (septet, J=7 Hz, 1H), 7.20–7.85 (m, 3H), 9.11 (br s, 1H); Analysis for $C_{10}H_{12}N_2O_3SCl_2$: Theory: C, 38.60; H, 3.89; N, 9.00; Found: C, 38.82; H, 3.62; N, 8.80.

EXAMPLE 8

Preparation of N-(4-chloro-3-trifluoromethylphenyl)-N'-2-propanesulfonylurea 2-propanesulfonamide sodium salt (4.35 g) in THF (200 ml) was combined with 4-chlorophenyl isocyanate (6.65 g) in THF (50 ml). The mixture was stirred overnight at room temperature. After evaporating the solvent and adding water, the mixture was filtered and the water removed under vacuum. The solid was dissolved in water, the mixture acidified, and the resulting precipitate recovered by filtration to provide 7.4 g of solid with a melting point of 135–40° C.

NMR: 60 MHz DMSO 1.33 (d, J=7 Hz, 6H), 3.77 (m, 1H), 7.67 (m, 2H), 8.03 (m, 1H), 9.33 (br s, 1H); Analysis for $C_{11}H_{12}O_3N_2SClF_3$: Theory: C, 38.32; H, 3.51; N, 8.13; Found: C, 38.53; H, 3.78; N, 7.89.

EXAMPLE 9

Preparation of N-(4-chlorophenyl)-N'-1-butanesulfonylurea 1-butanesulfonamide sodium salt (9.1 g, 57 mmole) was dissolved in water (40 ml) and acetone (40 ml) was added. To the resulting mixture was added dropwise 40 ml of acetone containing 4-chlorophenyl isocyanate (8.6 g). After two hours solid was removed from the reaction mixture by filtration. The solid was washed with water and the combined filtrate was treated with 1N HCl (57 ml). After about one hour, precipitate was collected from the filtrate and washed with water. After drying at 65° C. under vacuum, 10.7 g of product were obtained.

NMR: 300 MHz DMSO 0.89 (t, J=8 Hz, 3H), 1.41 (sextet, J=8 Hz, 2H), 1.68 (pentet, J=8 Hz, 2H), 3.44 (t, J=8 Hz, 2H), 7.42 (ABq, J=9 Hz, Δv=27 Hz, 4H) 8.97 (s, 1H), 10.24 (v br s, 1H); MS: 290 (M+); Analysis for $C_{11}H_{15}N_2O_3ClS$: Theory: C, 45.44; H, 5.20; N, 9.63; S, 11.03; Found: C, 45.40; H, 5.20; N, 9.88; S, 11.05.

EXAMPLE 10

Preparation of N-(4-fluorophenyl)-N'-2-butanesulfonylurea

The general method of procedure B was followed with 2-butanesulfonamide (6.85 g), sodium methoxide (2.7 g), methanol (250 ml), and 4-fluorophenyl isocyanate (6.8 g) except 1N HCl was added to provide the free urea. The solid was recrystallized from benzene to provide 5.2 g of white powder with a melting point of 136–138° C.

NMR: 60 MHz DMSO 0.95 (t, J=7 Hz, 3H), 1.28 (d, J=7 Hz, 3H), 1.74 (m, 2H), 3.51 (m, 1H), 6.95–7.60 (m, 4H), 8.80 (br s, 1H); Analysis for $C_{11}H_{15}N_2O_3SF$: Theory: C, 48.16; H, 5.51; N, 10.21; Found: C, 48.19; H, 5.77; N, 9.98.

EXAMPLE 11

Preparation of N-(4-chlorophenyl)-N'-2-butanesulfonylurea

The method of Example 10 was followed with 2-butanesulfonamide (6.85 g), methanol (250 ml), sodium methoxide (2.7 g), tetrahydrofuran (250 ml) and 4-chlorophenyl isocyanate (7.7 g) with the resulting solid being recrystallized from ethyl acetate to give 2.7 g of white crystals with a melting point of 172–174° C.

NMR: 60 MHz DMSO 1.00 (t, J=7 Hz, 3H), 1.34 (d, J=7 Hz, 3H), 1.40–2.20 (m, 2H), 3.50 (m, 1H), 7.46 (m, 4H), 8.97 (br s, 1H) Analysis for $C_{11}H_{15}N_2O_3SCl$: Theory: C, 45.44; H, 5.20; N, 9.63; Found: C, 45.22; H, 5.33; N, 9.59.

EXAMPLE 12

Preparation of N-(4-bromophenyl)-N'-2-butanesulfonylurea

The general method of procedure A was followed with 2-butanesulfonamide (10 g, 73 mmole), 1N sodium hydroxide (73 ml), and 4-bromophenyl isocyanate (13.7 g). The filtrate from the reaction mixture was treated with 1N HCl and the resulting precipitate redissolved in 1N sodium hydroxide and reprecipitated with 1N HCl. The solid product was collected and dried at 65° C. under vacuum. The dissolution and precipitation procedure was repeated to provide 13.0 g of product which had the following analysis.

NMR: 300 MHz DMSO 0.98 (t, J=8 Hz, 3H), 1.30 (d, J=7 Hz, 3H), 1.54 (m, 1H), 1.94 (m, 1H), 3.54 (m, 1H), 7.44 (ABq, J=9 Hz, Δv=29 Hz, 4H), 9.00 (s, 1H), 10.34 (v br s, 1H); MS: 334, 336 (M+'s for Br isotopes); Analysis for $C_{11}H_{15}N_2O_3SBr$: Theory: C, 39.41; H, 4.51; N, 8.36; S, 9.57; Found: C, 39.14; H, 4.27; N, 8.62; S, 9.31.

EXAMPLE 13

Preparation of N-(3,4-dichlorophenyl)-N'-2-butanesulfonylurea

The general method of procedure A was followed using 2-butanesulfonamide (10 g), 1N sodium hydroxide (73 ml) and 3,4-dichlorophenyl isocyanate (13 g). 1N HCl was added and after removal of the acetone the solid was diluted with water, collected, and dried at 65° C. under vacuum. The solid was recrystallized in acetone and hexane to provide 5.2 g of product.

NMR: 300 MHz DMSO 1.00 (t, J=8 Hz, 3H), 1.31 (d, J=8 Hz, 3H), 1.54 (m, 1H), 1.94 (m, 1H), 3.55 (m, 1H), 7.36 (dd, J=3,9 Hz, 1H), 7.57 (d, J=9 Hz, 1H), 7.81 (d, J=3 Hz, 1H), 9.14 (s, 1H), 10.53 (v br s, 1H) MS: 324, 326 (M+'s for Cl isotopes) Analysis for $C_{11}H_{14}Cl_2N_2O_3S$: Theory: C, 40.63; H, 4.34; N, 8.61; S, 9.86; Found: C, 40.47; H, 4.22; N, 8.67; S, 9.99.

EXAMPLE 14

Preparation of N-(4-chlorophenyl)-N'-(2-methyl-1-propane)sulfonylurea sodium salt The general method of procedure B was followed with 2-methyl-1-propanesulfonamide (6.0 g) and sodium methoxide (2.3 g), tetrahydrofuran (200 ml), and 4-chlorophenyl isocyanate (6.7 g). 8.8 g of white powder product was obtained having a melting point greater than 260° C.

NMR: 60 MHz DMSO 1.00 (d, J=7 Hz 6H), 2.10 (m, 1H), 2.90 (d, J=6 Hz, 2H), 7.38 (ABq, J=9 Hz, Δv=26 Hz, 4H), 8.50 (br s, 1H); Analysis for $C_{11}H_{14}N_2O_3SCl \cdot Na$ Theory: C, 42.24; H, 4.51; N, 8.96; Found: C, 42.52; H, 4.52; N, 9.06.

EXAMPLE 15

Preparation of N-(4-chlorophenyl)-N'-1-pentanesulfonylurea

The general method of procedure A was followed with 1-pentanesulfonamide (10 g), acetone (200 ml), 1N NaOH (66 ml) and 4-chlorophenyl isocyanate (9.6 g). 1N HCl (66 ml) was used to acidify the solution. Additional water was added and after standing overnight the solid was isolated and dried to provide 14 g of product.

NMR: 300 MHz DMSO 0.87 (t, J=7 Hz, 3H), 1.22–1.44 (m, 4H), 1.70 (m, 2H), 3.44 (t, J=8 Hz, 2H), 7.41 (ABq, J=9 Hz, Δv=27 Hz, 4H), 8.99 (s, 1H), 10.25 (v br s, 1H); MS: 305 (M+1); Analysis for $C_{12}H_{17}N_2O_3SCl$: Theory: C, 47.29; H, 5.62; N, 9.19; S, 10.52; Found: C, 47.06; H, 5.54; N, 9.37; S, 10.36.

EXAMPLE 16

Preparation of N-(4-chlorophenyl)-N'-(2-ethoxyethane)sulfonylurea

The general method of procedure A was followed with 2-ethoxyethanesulfonamide (5 g, 32.6 mmole), acetone (100 ml), 1N sodium hydroxide (33 ml) and 4-chlorophenyl isocyanate (4.75 g). The reaction mixture was acidified with 1N HCl (33 ml). The solid product was dried at 65° C. under vacuum to provide 9.5 g of white solid.

NMR: 300 MHz DMSO 1.04 (t, J=7 Hz, 3H), 3.42 (q, J=7 Hz, 2H), 3.73 (m, 4H), 7.41 (ABq, J=9 Hz, Δv=27 Hz, 4H), 8.90 (s, 1H), 10.10 (v br s, 1H); MS: 306 (M+); Analysis for $C_{11}H_{15}N_2O_4SCl$: Theory: C, 43.07; H, 4.93; N, 9.13; S, 10.45; Found: C, 43.01; H, 4.91; N, 8.98; S, 10.42.

EXAMPLE 17

Preparation of N-(4-chlorophenyl)-N'-3-pentanesulfonylurea

The general method of procedure A was followed with 3-pentanesulfonamide (10 g), acetone (300 ml), 1N sodium hydroxide (56 ml), and 4-chlorophenyl isocyanate (9.6 g) dissolved in 70 ml of acetone. After two hours of stirring, 1N HCl (66 ml) was added followed by more water. The acetone was stripped off, and the resulting solid collected, to give, after drying at 65° C. under vacuum, 13.1 g of product.

NMR: 300 MHz DMSO 1.00 (t, J=8 Hz, 6H), 1.73 (m, 2H), 1.89 (m, 2H), 3.44 (m, 1H), 7.41 (ABq, J=9 Hz, Δv=27 Hz, 4H), 8.93 (s, 1H), 10.33 (v br s, 1H); MS: 305 (M+1);

Analysis for $C_{12}H_{17}N_2O_3SCl$: Theory: C, 47.29; H, 5.62; N, 9.19; S, 10.52; Found: C, 47.10; H, 5.57; N, 8.94; S, 10.55.

EXAMPLE 18

Preparation of N-(4-chlorophenyl)-N'-3-methyl-1-butanesulfonylurea

The general method of procedure A was used with 3-methyl-1-butanesulfonamide (10 g), 1N sodium hydroxide (66 ml), acetone (66 ml), and 4-chlorophenyl isocyanate (9.9 g) dissolved in acetone (66 ml). After two hours the filtrate from the reaction mixture was treated with 1N HCl (66 ml) followed by the addition of more HCl to provide a precipitate which was dried at 65° C. under vacuum yielding 7.3 g of solid.

NMR: 300 MHz DMSO 0.90 (d, J=7 Hz, 6H), 1.55–1.75 (m, 3H), 3.45 (m, 2H), 7.42 (ABq, J=9 Hz, Δv=27 Hz, 4H), 8.98 (s, 1H), 10.29 (v br s, 1H); MS: 304 (M+); Analysis for $C_{12}H_{17}N_2O_3SCl$: Theory: C, 47.29; H, 5.62; N, 9.19; S, 10.52; Found: C, 47.37; H, 5.54; N, 8.95; S, 10.27.

EXAMPLE 19

Preparation of N-(4-fluorophenyl)-N'-cyclopentanesulfonylurea

The general method of procedure B was followed with cyclopentanesulfonamide (7.45 g), sodium methoxide (2.7 g), methanol (200 ml), tetrahydrofuran (200 ml), and 4-fluorophenyl isocyanate (6.85 g). The residue was dissolved in water and the solution acidified with 1N HCl. The resulting solid was separated and recrystallized from benzene to give 2.9 g of white solid with a melting point of 155–157° C.

NMR: 60 MHz DMSO 1.60–2.30 (m, 8H), 4.22 (m, 1H), 7.10–7.80 (m, 4H), 8.98 (br s, 1H); Analysis for $C_{12}H_{15}N_2O_3SF$: Theory: C, 50.34; H., 5.28; N, 9.78; Found: C, 50.11; H, 5.01; N, 9.60.

EXAMPLE 20

A. Preparation of N-(4-chlorophenyl)-N'-cyclopentanesulfonylurea sodium salt

The general method of procedure B was followed with cyclopentanesulfonamide (7.45 g), sodium methoxide (2.7 g), methanol (206 ml), tetrahydrofuran (200 ml), and 4-chlorophenyl isocyanate (7.7 g). After stirring overnight, the recovered solid was dissolved in water and filtered. The water was removed by evaporation and the solid recrystallized from water to give 8.0 g of white crystals which decomposed at 261° C.

NMR: 60 MHZ DMSO 1.40–2.10 (m, 8H), 3.65 (m, 1H), 7.37 (ABq, J=9 Hz, Δv=26 Hz, 4H), 8.48 (s, 1H); Analysis for $C_{12}H_{14}N_2O_3SCl\cdot Na$: Theory: C, 44.38; H, 4.35; N, 8.63; Found: C, 44.16; H, 4.48; N, 8.54.

B. Preparation of N-(4-chlorophenyl)-N'-cyclopentanesulfonylurea

Cyclopentanesulfonamide (9.7 g) was dissolved in acetone (300 ml) and 1N NaOH (65 ml) was added. To the resulting solution was added p-chlorophenylisocyanate (9.5 g) dissolved in acetone (100 ml). The solution was allowed to stir for two hours and was then treated with 1N HCl (65 ml). The resulting solid was collected and treated with 1N NaOH (100 ml). This mixture was treated with 1N HCl (100 ml) and the resulting solid collected. The solid was dissolved in acetone, water was added and the acetone was stripped off. The solid material was collected and dried to provide 12.8 g of product.

NMR: 300 MHz DMSO 1.55–1.75 (m, 4H), 1.83–2.03 (m, 4H), 4.08 (pentet, J=8 Hz, 1H), 7.41 (ABq, J=8 Hz, Δv=28 Hz, 4H), 8.95 (s, 1H), c. 10.35 (v br s, 1H); MS: 302 (M+); Analysis for $C_{12}H_{15}ClN_2O_3S$: Theory: C, 47.60; H, 4.99; N, 9.25; S, 10.59; Found: C, 47.81; H, 4.95; N, 9.10; S, 10.36.

EXAMPLE 21

Preparation N-(4-bromophenyl)-N'-cyclopentanesulfonylurea

The general method of procedure A was followed with cyclopentanesulfonamide (3 g), acetone (100 ml), 1N sodium hydroxide (21 ml), and 4-bromophenyl isocyanate (3.7 g) dissolved in acetone (50 ml). After two hours, 1N HCl (21 ml) was added. The resulting precipitate was collected, washed with water and dried at 60° C. under vacuum to provide 5.4 g of product.

NMR: 300 MHz DMSO 1.53–1.77 (m, 4H), 1.97 (m, 4H), 4.08 (pentet, J=9 Hz, 1H), 7.46 (ABq, J=9 Hz, Δv=29 Hz, 4H), 8.97 (s, 1H), 10.32 (v br s, 1H); MS: 346, 348 (M+'s for Br isotopes); Analysis for $C_{12}H_{15}N_2O_3SBr$: Theory: C, 41.51; H, 4.35; N, 8.07; S, 9.23; Found C, 41.78; H, 4.13; N, 7.91; S, 9.40.

EXAMPLE 22

Preparation of N-(3,4-dichlorophenyl)-N'-cyclopentanesulfonylurea

The general method of procedure A was followed with cyclopentanesulfonamide (3 g), acetone (200 ml), 1N sodium hydroxide (20 ml), and 3,4-dichlorophenyl isocyanate (3.6 g) dissolved in acetone (50 ml). After two hours, 1N HCl (20 ml) was added and the resulting solid diluted with water and collected. After drying at 65° C., 5.5 g of solid product were obtained.

NMR: 300 MHz DMSO 1.57–1.77 (m, 4H), 1.97 (m, 4H), 4.08 (pentet, J=9 Hz, 1H), 7.37 (dd, J=3.10, 1H), 7.58 (d, J=10, 1H), 7.81 (d, J=3 1H), 9.14 (s, 1H), 10.55 (v br s, 1H); MS: 336, 338 (M+'s for Cl isotopes); Analysis for $C_{12}H_{14}Cl_2N_2O_3S$: Theory: C, 42.74; H, 4.18; N, 8.31; S, 9.51; Found: C, 42.80; H, 4.18; N, 8.19; S, 9.46.

EXAMPLE 23

Preparation of N-(4-chlorophenyl)-N'-1-hexanesulfonylurea

The general method of procedure A was followed with hexanesulfonamide (10 g), acetone (200 ml), 1N sodium hydroxide (60 ml), and 4-chlorophenyl isocyanate (8.8 g) in acetone (50 ml). After three hours of stirring, 1N HCl (60 ml) was added followed by removal of acetone and collection of solid from the water. The solid was washed with water and dried at 65° C. under vacuum to provide 16 g of product.

NMR: 300 MHz DMSO 0.86 (t, J=7 Hz, 3H), 1.20–1.48 (m, 6H), 1.71 (m, 2H), 3.44 (t, J=8 Hz, 2H), 7.41 (ABq, J=9 Hz, Δv=27 Hz, 4H), 8.98 (s, 1H), 10.07 (v br s, 1H); MS: 319 (M+1); Analysis for $C_{13}H_{19}ClN_2O_3S$: Theory: C, 48.97; H, 6.01; N, 8.79; S, 10.06; Found: C, 49.21; H, 5.94; N, 9.04; S, 10.13.

EXAMPLE 24

Preparation of N-(4-chlorophenyl)-N'-cyclohexanesulfonylurea

The general method of procedure A was followed with cyclohexanesulfonamide (1.89 g), acetone (5 ml), 1N sodium hydroxide (11.6 ml). After stirring overnight at room temperature, the mixture was cooled in an ice bath and 4-chlorophenyl isocyanate (1.89 g) dissolved in acetone (5 ml) was added. The mixture was warmed to room temperature and stirred two days, filtered, and the separated white solid washed with water. The filtrates were combined and treated with glacial acetic acid (1 ml) followed by addition of water. The resulting solid was collected by filtration, washed with water and air dried to provide 2.57 g of a tan powder.

NMR: 270 MHz DMSO 1.05–2.15 (m, 10H), 3.45 (m, 1H), 7.40 (ABq, J=9 Hz, Δv=30 Hz, 4H), 8.93 (s, 1H); Analysis for $C_{13}H_{17}N_2O_3SCl$: Theory: C, 49.29; H, 5.41; N, 8.84; S, 10.12; Found: C, 48.94; H, 5.27; N, 8.68; S, 9.92.

EXAMPLE 25

Preparation of N-(3,4-dichlorophenyl)-N'-cyclohexanesulfonylurea sodium salt

Cyclohexanesulfonamide (6.52 g) in THF (200 ml) was treated with NaH (2.15 g) and stirred 3 hours. 3,4-Dichlorophenylisocyanate (7.52 g) dissolved in THF (50 ml) was added dropwise, and the mixture stirred overnight. The solvent volume was reduced to approximately 50 ml, and the resulting solid collected and recrystallized from isopropanol/water, to give 5.0 g product. Melting point 260° C.

NMR: 60 MHz DMSO 0.80–2.20 (m, 10H), 3.00 (m, 1H), 7.34 (m, 2H), 7.98 (m, 1H), 8.68 (br s, 1H); Analysis for $C_{13}H_{15}N_2O_3SCl_2 \cdot Na$: Theory: C, 41.84; H, 4.05; N, 7.51; Found: C, 41.64; H, 4.29; N, 7.30.

EXAMPLE 26

Preparation of N-(4-chlorophenyl)-N'-1-(but-1-ene) sulfonylurea

A. Preparation of N-(t-butyl)-methanesulfonamide t-Butylamine (105 ml, 1.0 mole) was dissolved in THF (about 950 ml) and cooled to 0° C. Methanesulfonylchloride (57.2 g) was added and the solution allowed to warm to room temperature overnight. The mixture was filtered and the filtrate stripped to dryness. The resulting residue was dissolved in methylene chloride and washed with 1N HCl followed by washing first with water and then with brine (water saturated with NaCl). The methylene chloride layer was dried over $Na_2SO_4$, filtered, and stripped to dryness. The resulting residue was dissolved in pentane, and the solid which crystallized was collected and dried.

$^1$H NMR: 300 MHz ($d_6$-DMSO) δ 1.23 (s, 9H), 2.90 (s, 3H), 6.79 (br s, 1H).

B. N-(t-Butyl)-2-hydroxy-1-butanesulfonamide

The product from 26A above (11.3 g) was dissolved in THF (about 400 ml) under argon and cooled to −78° c. n-Butyllithium (140 ml, 1.6 M) was added dropwise and the mixture stirred at 0° C. for one hour. The mixture was then cooled to −78° C. and propionaldehyde (6.6 g, 8.3 ml) in THF (40 ml) was added over a period of about 15 minutes. The solution was allowed to warm to room temperature under argon over-night. The mixture was then cooled to 0° C. and treated with 1N HCl (400 ml). The aqueous layer was separated and extracted with ethyl ether. The combined organic layers were washed with water, dried over $Na_2SO_4$, filtered, and then stripped to dryness. The residue was passed through a silica column using a solvent gradient of 20% ethyl acetate in hexane to 50% ethyl acetate in hexane. Fractions containing product were treated with pentane to obtain a crystalline product.

$^1$H NMR: 300 MHz (CDCl$_3$) δ 0.99 (t, J=8 Hz, 3H), 1.40 (s, 9H), 1.46–1.70 (m, 2H), 3.08–3.40 (m, 3H), 4.06–4.16 (m, 1H), 4.36 (v br s, 1H); MS: 209 (M+); Analysis for $C_8H_{19}NO_3S$: Theory: C, 45.91; H, 9.15; N, 6.69; Found: C, 45.71; H, 8.96; N, 6.72.

C. N-(t-Butyl)-1-butene-1-sulfonamide

The product from 26B above (2 g) was dissolved in methylene chloride (100 ml) and triethylamine (4 ml) was added. The solution was cooled under nitrogen with an ice bath as methanesulfonyl chloride (1.1 ml) was added. The mixture was allowed to warm to room temperature for an hour and was then heated to reflux for four hours. The mixture was stirred at room temperature overnight and then refluxed for an additional seven hours. The mixture was allowed to stir at room temperature overnight and then washed with 1N HCl followed by three water washings. The resulting methylene chloride layer was dried over $Na_2SO_4$, filtered and then stripped to provide 2 g of a residue. This material was passed through a silica column using 20% ethyl acetate in hexane to provide 1.46 g of product.

$^1$H NMR: 300 MHz (CDCl$_3$) δ 1.08 (t, J=8 Hz, 3H), 1.33 (s, 9H), 2.24 (m, 2H), 6.23 (m, 1H), 6.77 (m, 1H).

D. 1-Butene-1-sulfonamide

The product from 26C above (1.2 g) was dissolved in trifluoroacetic acid (30 ml) and allowed to stir at room temperature overnight. The solution was evaporated and the resulting residue recrystallized from a mixture of methylene chloride and hexane to provide 0.75 g of product.

$^1$H NMR: 300 MHz (CDCl$_3$) δ 1.11 (t, J=8 Hz, 3H), 2.27 (pentet, J=7 Hz, 2H), 4.70 (br s, 2H), 6.37 (d, J=15 Hz, 1H), 6.88 (dt, J=15, 6 Hz, 1H); MS: 135 (M+); Analysis for $C_4H_9NO_2S$: Theory: C, 35.54; H, 6.71; N, 10.36; S, 23.72; Found: C, 35.74; H, 6.71; N, 10.36; S, 23.64.

E. N-(4-Chlorophenyl)-N'-1-(but-1-ene)sulfonylurea

The general method of procedure A was followed with 1-butene-1-sulfonamide from 26D above (0.75 g), acetone (50 ml), 1N sodium hydroxide (5.6 ml), and 4-chlorophenyl isocyanate (0.8 g) dissolved in acetone. After about four hours, the solvent was removed and the residue mixed with water and then treated with 1N HCl (5.7 ml). After stirring overnight at room temperature, the solid was collected and dried under vacuum and then recrystallized in a mixture of toluene and hexane to provide 1.1 g of solid product.

NMR: 300 MHz CDCl$_3$ 1.10 (t, J=8 Hz, 3H), 2.32 (m, 2H), 6.42 (d, J=14, 1H), 7.06 (dt, J=14,6 Hz, 1H), 7.33 (ABq, J=10 Hz, Δv=30 Hz, 4H), 7.47 (br s, 1H), 8.35 (br s, 1H); MS: 288 (M+); Analysis for $C_{11}H_{13}N_2O_3SCl$: Theory: C, 45.76; H, 4.54; N, 9.70; S, 11.10; Found: C, 45.90; H, 4.50; N, 9.72; S, 11.18.

EXAMPLE 27

Preparation of N-(4-chlorophenyl)-N'-2-(but-2-ene) sulfonylurea

A. N-(t-Butyl)ethanesulfonamide t-Butylamine (150 ml) was dissolved in THF (500 ml) and cooled with an ice bath as ethanesulfonyl chloride (75 ml) dissolved in THF (about 200 ml) was added dropwise. The mixture was allowed to warm to room temperature and stirred overnight. The mixture was stripped to dryness and 1N HCl was added. The solution was extracted with methylene chloride and the extract washed two times with water. The methylene chloride layer was dried over $Na_2SO_4$, filtered, and the methylene chloride removed by vacuum. The resulting oil was passed through a silica column eluting with a mixture of ethyl ether and methylene chloride. Recrystallization from a mixture of methylene chloride and hexane provided 49.1 of product.

¹H NMR: 300 MHz (CDCl₃) δ 1.36 (t, J=7 Hz, 3H), 1.38 (s, 9H), 3.06 (q, J=7 Hz, 2H), 4.13 (v br s, 1H); MS: 165 (M+); Analysis for $C_6H_{15}NO_2S$: Theory: C, 43,61; H, 9.15; N, 8.48; S, 19.40; Found: C, 43.41; H, 8.88; N, 8.35; S, 19.22.

B. N-(t-Butyl)-3-hydroxy-2-butanesulfonamide

The product from 27A above (25 g) was dissolved in THF (about 470 ml) and cooled to −78° C. under argon. n-Butyllithium (208 ml, 1.6 molar) was added dropwise. The reaction mixture was allowed to warm to room temperature and stirred for one hour. The mixture was then cooled to −78° C. and acetaldehyde (10.2 ml) dissolved in THF (20 ml) was added and the solution allowed to stir at room temperature overnight. The mixture was cooled to 0° C. and 1N HCl (600 ml) was added. The resulting mixture was extracted with ethyl ether. The ether layer was washed with water and dried over $Na_2SO_4$. The ether was removed and the resulting residue passed through a silica column eluting with a mixture of ethyl acetate and hexane (25:75) to provide 16.84 g of product (1:1 mixture of two diastereomers).

¹H NMR: 300 MHz (CDCl₃) δ 1.24–1.35 (m, 6H), 1.39+1.40 (two s, 9H), 2.92–3.07 (m, 1H), 4.16+4.53 (two m, 1H); MS: 209 (M+); Analysis for $C_8H_{19}NO_3S$: Theory: C, 45.91; H, 9.15; N, 6.69; S, 15.32; Found: C, 45.67; H, 9.30; N, 6.43; S, 15.12.

C. N-(t-Butyl)-2-butene-2-sulfonamide

The product from 27B above (16.84 g) was dissolved in methylene chloride (600 ml) and triethylamine (34 ml) was added. The resulting solution was cooled to 0° C. and methanesulfonyl chloride (9.3 ml) was added dropwise. The resulting solution was refluxed overnight, then washed with 1N HCl followed by water. The methylene chloride layer was dried over $Na_2SO_4$, filtered, and stripped to provide an oil. The oil was dissolved in toluene (500 ml) and triethylamine (36 ml) was added. The mixture was refluxed approximately 60 hours and then allowed to stand at room temperature for five days. The solvent was removed and the residue dissolved in methylene chloride which was then washed with 1N HCl. The methylene chloride layer was washed with water three times and dried over $Na_2SO_4$, filtered and stripped of solvent. The residue was passed over a silica column with fractions collected and analyzed by NMR. Three fractions showing highest purity product were combined to provide 6.2 g of product.

¹H NMR: 300 MHz (CDCl₃) δ 1.30 (s, 9H), 1.79 (d, J=7 Hz, 3H), 1.98 (s, 3H), 6.71 (q, J=7 Hz, 1H); MS: 191 (M+); Analysis for $C_8H_{17}NO_2S$: Theory: C, 50.23; H, 8.96; N, 7.32; S, 16.76; Found: C, 50.14; H, 8.99; N, 7.19; S, 17.01.

D. 2-Butene-2-sulfonamide

The product from 27C above (6.2 g) was combined with trifluoroacetic acid (100 g) and stirred at room temperature for 36 hours. The mixture was stripped to dryness and the residue passed through a silica column eluting with a solvent gradient of methylene chloride to 3% methanol in methylene chloride. Fractions were collected and analyzed by NMR. Three fractions were combined and recrystallized from toluene four times. Removal of the solvent provided 2.1 g of product.

¹H NMR: 300 MHz (CDCl₃) δ 1.80 (d, J=7 Hz, 3H), 2.03 (s, 3H), 4.58 (br s, 2H), 6.73 (q, J=7 Hz, 1H); MS: 135 (M+);

E. Preparation of N-(4-chlorophenyl)-N'-2-(but-2-ene) sulfonylurea

The general method of procedure A was followed with 2-butene-2-sulfonamide (2.08 g) from 27D above, acetone (30 ml), 1N sodium hydroxide (15.4 ml), and 4-chlorophenyl isocyanate (2.25 g) dissolved in acetone (30 ml). After about two hours, 1N HCl (16 ml) was added. The acetone was removed and after standing overnight the solid was collected and then dried in vacuum. The solid was recrystallized from a mixture of dichloromethane, acetonitrile and hexane to provide 3.25 g of product.

NMR: 300 MHz CDCl₃/DMSO 1.86 (d, J=8 Hz, 3H), 2.03 (s, 3H), 6.89 (q, J=8 Hz, 1H), 7.29 (ABq, J=9 Hz, Δv=43 Hz, 4H), 8.28 (s, 1H), 9.97 (s, 1H); MS: 288 (M+); Analysis for $C_{11}H_{13}N_2O_3SCl$: Theory: C, 45.76; H, 4.54; N, 9.70; S, 11.10; Found: C, 45.53; H, 4.54; N, 9.60; S, 11.18.

EXAMPLE 28

Preparation of N-(4-chlorophenyl)-N'-phenylmethanesulfonylurea

The general method of procedure A was followed with phenylmethanesulfonamide (51.3 g), acetone (30 ml), 1N sodium hydroxide (31.5 ml), and 4-chlorophenyl isocyanate (5.07 g) in acetone (30 ml). The reaction mixture was filtered and the filtrate acidified with 1N HCl (31.5 ml). The solid product was washed with water and dried in vacuum at 60° C. to provide 7.73 g of white powder.

NMR: 270 MHz DMSO 4.78 (s, 2H), 7.35–7.54 (m, 9H), 8.88 (s, 1H), 10.20 (v br s, 1H); MS: 324 (M+); Analysis for $C_{14}H_{13}N_2O_3SCl$: Theory: C, 51.77; H, 4.03; N, 8.63; S, 9.87; Found: C, 51.83; H, 3.86; N, 8.56; S, 10.04.

EXAMPLE 29

Preparation of N-(4-chlorophenyl)-N'-(2-phenyl)-ethenesulfonylurea

The general method of procedure A was followed with 2-phenylethenesulfonamide (2.75 g), acetone (16 ml), 1N sodium hydroxide (16 ml), with first water (32 ml) then acetone (32 ml) added, followed by 4-chlorophenyl isocyanate (2.61 g) in acetone (16 ml). After stirring at room temperature overnight, a solid was removed by filtration and the filtrate was acidifed with 1N HCl (16 ml). Water (100 ml) was added and the solid was collected by filtration, washed with water and dried at 60° under vacuum to provide 3.5 g of product.

NMR: 270 MHz DMSO 7.30–7.90 (m, 11H), 9.00 (s, 1H), 10.53 (v br s, 1H); MS: 336 (M+); Analysis for $C_{15}H_{13}N_2O_3SCl$: Theory: C, 53.49; H, 3.89; N, 8.32; S, 9.52; Found: C, 53.77; H, 4.07; N, 8.13; S, 9.29.

EXAMPLE 30

Preparation of N-(4-chlorophenyl)-N'-phenylthiomethanesulfonyl urea

The general method of procedure A was used with phenylthiomethanesulfonamide (2.17 g), acetone (50 ml), 1N sodium hydroxide (10.7 ml), and 4-chlorophenyl isocyanate (1.55 g) in acetone (50 ml). After two hours, the acetone was removed, water was added followed by 1N HCl (11 ml). The resulting precipitate was washed with water and dried at 65° C. under vacuum to provide 3.4 g of solid.

NMR: 300 MHz DMSO 4.97 (s, 2H), 7.16–7.37 (m, 7H), 7.56 (d, J=8 Hz, 2H), 8.84 (s, 1H), c. 10.4 (v br s, 1H); MS: 356 (M+); Analysis for $C_{14}H_{13}N_2O_3S_2Cl$: Theory: C, 47.12; H, 3.67; N, 7.85; S, 17.97; Found: C, 47.10; H, 3.57; N, 7.74; S, 17.79.

The compounds of Formula I have been shown to be active against transplanted mouse tumors in vivo. The compounds were tested in C3H mice bearing a 6C3HED lymphosarcoma, also known as the Gardner lymphosarcoma (GLS). The 6C3HED lymphosarcoma was obtained from the Division of Cancer Treatment, National Cancer Institute, Tumor Bank, maintained at E. G. and G. Mason Research (Worcester, Mass.). First passage tumor was stored in liquid nitrogen using standard techniques. The transplanted tumor was re-established from the Tumor Bank every six months or as needed. The tumor was maintained by serial passage twice weekly in C3H mice.

In the procedure the tumor was removed from passage animals and minced into 1- to 3-mm square fragments using sterile techniques. Tumor pieces were checked for sterility using both Antibiotic Medium 1 and Brain Heart Infusion (Difco, Detroit, Mich.). Recipient mice were shaved and tumor pieces were implanted subcutaneously in the auxiliary region by trocar. Drug therapy on the appropriate schedule was initiated on the day after tumor implant. The compound being tested was mixed with 2.5 weight % of a polyoxy-ethylated castor oil known as "Emulphor EL-620" surfactant from GAF Chemicals Corporation (1:40 dilution of Emulphor in saline). All animals were weighed at the beginning and end of administration of the subject compounds. Food and water were provided ad libitum. The drug was administered orally in 0.5 ml of 2.5% Emulphor. Unless otherwise indicated, the compound was administered once per day for eight days. The tumor was measured the day after treatment ended with two dimensional measurements (width and length) of the tumor taken using Vernier calipers. Tumor weights were calculated from these measurements using the following formula:

Tumor weight (mg)=[tumor length (mm)×tumor width (mm)]$^2$ divided by 2

At least one control group of an equal number of mice was treated with the same volume of 2.5% Emulphor only. The percent inhibition was calculated by subtracting the ratio of the mean tumor size of the test group relative to the control group from 1 and multiplying the result by 100.

The results of administering some of the present compounds orally (unless otherwise indicated) to mice bearing a 6C3HED tumor are provided in the Table. In the Table, column 1 gives the example number corresponding to the preparation of the particular compound, column 2 provides the dose level, column 3 lists the percent inhibition of tumor growth, and column 4 gives the number of mice which died relative to the total number of animals in the group.

TABLE

| Example No. | Dose[1] | Percent Inhibition[2] | Toxic/Total[3] |
|---|---|---|---|
| 1 | 300.0 | — | 7/7 |
|   | 150.0 | — | 6/7 |
|   | 75.0 | 26 | 0/7 |
|   | 37.5 | 0 | 0/7 |
| 2 | 300.0 | 22 | 0/7 |
|   | 150.0 | 11 | 0/7 |
| 3 | 300.0 | — | 6/6 |
|   | 150.0 | 45 | 0/7 |
|   | 300.0 | — | 10/10 |
|   | 150.0 | 76 | 2/10 |
| 4 | 300.0 | — | 7/7 |
|   | 150.0 | 63 | 0/7 |
| 5 | 300.0 | 23 | 0/7 |
|   | 150.0 | 17 | 0/7 |
| 6 | 300.0 | 52 | 0/6 |
|   | 150.0 | 35 | 0/7 |
| 7 | 300.0 | 69 | 1/7 |
|   | 150.0 | 31 | 1/7 |
| 8 | 300.0 | 54 | 0/7 |

TABLE-continued

| Example No. | Dose[1] | Percent Inhibition[2] | Toxic/Total[3] |
|---|---|---|---|
|   | 150.0 | 36 | 0/7 |
| 9 | 300.0 | — | 7/7 |
|   | 150.0 | 92 | 2/7 |
|   | 30.0[4] | 20 | 0/7 |
|   | 30.0[5] | 0 | 0/7 |
| 10 | 300.0 | 52 | 0/7 |
|   | 150.0 | 12 | 0/7 |
| 11 | 400.0[6] | — | 10/10 |
|   | 200.0[6] | 100 | 5/10 |
|   | 100.0[6] | 89 | 0/9 |
|   | 50.0[6] | 23 | 0/10 |
|   | 25.0[6] | 2 | 0/10 |
|   | 400.0 | 98 | 3/10 |
|   | 200.0 | 68 | 0/10 |
|   | 100.0 | 19 | 0/10 |
|   | 50.0 | 3 | 0/10 |
|   | 25.0 | 5 | 0/10 |
|   | 300.0 | 98 | 2/7 |
|   | 200.0[7] | 69 | 3/10 |
|   | 100.0[7] | 29 | 0/10 |
|   | 50.0[7] | 0 | 0/10 |
|   | 25.0[7] | 0 | 0/10 |
|   | 12.5[7] | 0 | 0/10 |
|   | 200.0[8] | 0 | 0/6 |
|   | 100.0[8] | 9 | 0/7 |
|   | 50.0[8] | 4 | 0/7 |
| 12 | 300.0 | 38 | 0/7 |
|   | 150.0 | 0 | 0/7 |
|   | 300.0 | 99 | 5/10 |
|   | 150.0 | 20 | 0/10 |
| 13 | 300.0 | 71 | 0/10 |
|   | 150.0 | 26 | 0/10 |
|   | 300.0 | 70 | 0/7 |
|   | 150.0 | 48 | 0/7 |
| 14 | 300.0 | — | 7/7 |
|   | 150.0 | 60 | 0/5 |
| 15 | 300.0 | — | 7/7 |
|   | 150.0 | 83 | 2/7 |
| 16 | 300.0 | 76 | 0/7 |
|   | 150.0 | 38 | 0/7 |
| 17 | 300.0 | 39 | 0/7 |
|   | 150.0 | 0 | 0/7 |
| 18 | 300.0 | — | 7/7 |
|   | 150.0 | — | 5/7 |
|   | 75.0 | 26 | 0/7 |
|   | 37.5 | 12 | 0/7 |
| 19 | 300.0 | 44 | 0/7 |
|   | 150.0 | 34 | 0/7 |
| 20A | 300.0 | 92 | 0/5 |
|   | 150.0 | 48 | 0/6 |
| 20B | 600.0 | — | 10/10 |
|   | 300.0 | — | 10/10 |
|   | 150.0 | 92 | 2/10 |
|   | 75.0 | 41 | 0/10 |
|   | 37.5 | 33 | 0/10 |
| 21 | 300.0 | — | 7/7 |
|   | 150.0 | 16 | 0/7 |
|   | 300.0 | 85 | 5/10 |
|   | 150.0 | 74 | 0/10 |
| 22 | 300.0 | 40 | 3/7 |
|   | 150.0 | 0 | 0/7 |
|   | 300.0 | — | 10/10 |
|   | 150.0 | 29 | 0/10 |
| 23 | 300.0 | 93 | 2/7 |
|   | 150.0 | 49 | 2/7 |
| 24 | 300.0 | 49 | 0/10 |
|   | 150.0 | 43 | 0/10 |
| 25 | 300.0 | 15 | 0/7 |
|   | 150.0 | 14 | 0/7 |
| 26 | 300.0 | 96 | 3/7 |
|   | 150.0 | 83 | 2/7 |
| 27 | 300.0 | 100 | 7/10 |
|   | 150.0 | 47 | 0/10 |
| 28 | 200.0[6] | 99 | 0/9 |
|   | 100.0[6] | 80 | 0/10 |
|   | 50.0[6] | 51 | 0/10 |

TABLE-continued

| Example No. | Dose[1] | Percent Inhibition[2] | Toxic/Total[3] |
|---|---|---|---|
|  | 25.0[6] | 35 | 0/10 |
|  | 12.5[6] | 20 | 0/10 |
|  | 300.0 | 95 | 1/10 |
|  | 150.0 | 73 | 0/10 |
|  | 300.0 | 68 | 0/10 |
|  | 150.0 | 46 | 0/10 |
|  | 300.0 | — | 10/10 |
|  | 150.0 | 82 | 0/10 |
| 30 | 300.0 | — | 7/7 |
|  | 150.0 | 78 | 0/7 |
|  | 150.0[6] | 81 | 5/10 |
|  | 75.0[6] | 16 | 0/10 |

(1) Dose in milligrams per kilogram of body weight per dose
(2) [1-(Mean tumor weight in test group/mean tumor weight in control group)]×100
(3) Number of mice which died during test period/total number of mice in test group.
(4) Tumor system tested was C3H mammary adenocarcinoma with the dose administered intraperitoneally in 0.5 ml 2.5% Emulphor daily for ten days.
(5) Tumor system tested was X5563 Plasma Cell Myeloma with the dose administered intraperitoneally in 0.5 ml 2.5% Emulphor daily for ten days.
(6) Compound administered twice daily for eight days with each dose of the indicated amount.
(7) Compound administered intraperitoneally in 0.5 ml 2.5% Emulphor.
(8) Compound administered as a continuous infusion at the rate of 2 ml per day for 5 days.

The compounds of Formula I are antineoplastic agents and the invention provides a method of treating susceptible neoplasms in mammals, particularly humans. The method comprises administering a compound by various routes including the oral, rectal, transdermal, subcutaneous, intravenous, intramuscular, or intranasal routes, being usually employed in the form of a pharmaceutical composition. It is a special feature of these compounds that they are effective following oral administration. It has been found that higher dosage levels can be obtained by oral administration than by direct systemic administration due to a higher toxic effect observed with systemic administration.

The present compounds are useful in treating solid tumors including carcinomas such as ovarian, non-small cell lung, gastric pancreatic, prostate, renal cell, breast, colorectal, small cell lung, melanoma and head and neck, and sarcomas such as Kaposil's sarcoma and rhabdomyosarcoma.

The instant compounds can be administered individually or in combination, preferably orally, and usually in the form of a pharmaceutical composition. Such compositions are prepared in a manner well known in the pharmaceutical art and comprise at least one active compound. Accordingly, the present invention also includes pharmaceutical compositions comprising as active ingredient certain compounds of Formula I associated with a pharmaceutically acceptable carrier, and the invention further comprises the method of treating susceptible neoplasms using the compositions containing as an active ingredient a compound of Formula I.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it may be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. The compositions of the invention can be formulated so as to provide quick, sustained or delayed release of the active ingredient after administration to the patient by employing procedures well known in the art.

The compositions are preferably formulated in a unit dosage form with each dosage normally containing from about 5 mg to about 1 g, more usually about 25 to about 800 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For example, dosages per day will normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active compounds any of the compound of Formula I. The examples are illustrative only and are not intended to limit the scope of the invention in any way.

Formulation 1
Hard gelatin capsules are prepared using the following ingredients:

| | Quantity (mg/capsule) |
|---|---|
| N-[[(4-chlorophenyl)amino]-carbonyl]-1-butanesulfonamide | 250 |
| Starch | 305 |
| Magnesium stearate | 5 |

The above ingredients are mixed and filled into hard gelatin capsules in 560 mg quantities.

| Formulation 2 | |
|---|---|
| A tablet formula is prepared using the ingredients below: | |
| | Quantity (mg/tablet) |
| N-[[(4-chlorophenyl)amino]-carbonyl]cyclopentanesulfonamide | 250 |
| Cellulose, microcrystalline | 400 |
| Colloidal silicon dioxide | 10 |
| Stearic acid | 5 |

The components are blended and compressed to form tablets each weighing 665 mg.

| Formulation 3 | |
|---|---|
| Tablets each containing 60 mg of active ingredient are made up as follows: | |
| N-[[(4-chlorophenyl)amino]-carbonyl]phenylmethanesulfonamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50–60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

| Formulation 4 | |
|---|---|
| Capsules each containing 80 mg of medicament are made as follows: | |
| N-[[(4-chlorophenyl)amino]carbonyl]-1-butene-1-sulfonamide | 80 mg |
| Starch | 109 mg |
| Magnesium stearate | 1 mg |
| Total | 190 mg |

The active ingredient, starch and magnesium stearate are blended, passed through a No. 20 mesh U.S. sieve, and filled into hard gelatin capsules in 190 mg quantities.

| Formulation 5 | |
|---|---|
| Suppositories each containing 225 mg of active ingredient are made as follows: | |
| N-[[(4-chlorophenyl)amino]carbonyl]-phenylthiomethanesulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 6 | |
|---|---|
| Suspensions each containing 50 mg of medicament per 5 ml dose are made as follows: | |
| N-[[(4-chlorophenyl)amino]carbonyl]-2-phenylethenesulfonamide | 50 mg |
| Xanthan qum | 4 mg |
| Sodium carboxymethyl cellulose (11%) Microcrystalline cellulose (89%) | 50 mg |
| Sucrose | 1.75 g |
| Sodium benzoate | 10 mg |
| Flavor | q.v. |
| Color | q.v. |
| Purified water to | 5 ml |

The medicament, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

| Formulation 7 | |
|---|---|
| Capsules each containing 150 mg of medicament are made as follows: | |
| N-[[(4-chlorophenyl)amino]carbonyl]-2-methyl-1-propanesulfonamide | 150 mg |
| Starch | 407 mg |
| Magnesium stearate | 3 mg |
| Total | 560 mg |

The active ngredient, starch and magnesium stearate are blended, passed through a No. 20 mesh U.S. sieve, and filled into hard gelatin capsules in 560 mg quantities.

| Formulation 8 | |
|---|---|
| A dry powder inhaler formulation is prepared containing the following components: | |
| | Weight % |
| N-[[(4-chlorophenyl)amino]-carbonyl]-2-butanesulfonamide | 5 |
| Lactose | 95 |

The active compound is mixed with the lactose and the mixture added to a dry powder inhaling appliance.

What is claimed is:

1. A compound useful in the treatment of susceptible neoplasms in mammals having the formula

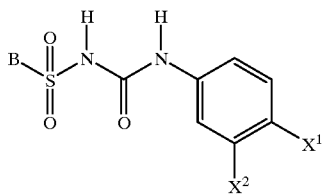

wherein
$X^1$ is halo;
$X^2$ is hydrogen, halo, or $CF_3$; and
wherein
B is:
- a) $C_2$–$C_7$ alkyl with the proviso that when B is n-butyl $X^2$ is other than hydrogen;
- e) a $C_5$–$C_6$ cycloalkyl; or
- f) $RZR^1$-where R is phenyl or $C_1$–$C_2$ alkyl, $R^1$ is $CH_2$ or $C_2H_4$, and Z is oxygen or sulfur; or pharmaceutically acceptable salts thereof.

2. The compound of claim 1 wherein $X^1$ is chloro, bromo, or fluoro; $X^2$ is chloro or $CF_3$;
B is:
- a) $C_2$–$C_7$ alkyl;
- e) a $C_5$–$C_6$ cycloalkyl; or
- f) $RZR^1$— where R is phenyl or $C_1$–$C_2$ alkyl, $R^1$ is $CH_2$ or $C_2H_4$, and Z is oxygen or sulfur; or pharmaceutically acceptable salts thereof.

3. The compound of claim 1 selected from the group consisting of N-[[3-chloro-4-fluorophenyl)amino]carbonyl]-2-propanesulfonamide; N-[[(3,4-dichlorophenyl)amino]carbonyl]-2-propanesulfonamide; N-[[(3-trifluoromethyl-4-chlorophenyl)amino]carbonyl]-2-propanesulfonamide; N-[[(4-chlorophenyl)amino]carbonyl]cyclohexanesulfonamide; N-[[(4-bromophenyl)amino]carbonyl]cyclopentanesulfonamide; N-[[(4-chlorophenyl)amino]carbonyl]-2-ethoxyethanesulfonamide; N-[[(3,4-dichlorophenyl)amino]carbonyl]-2-butanesulfonamide; N-[[(4-fluorophenyl)amino]carbonyl]cyclopentanesulfonamide; N-[[(4-chlorophenyl)amino]carbonyl]cyclopentanesulfonamide; N-[[(4-chlorophenyl)amino]carbonyl]phenylthiomethaniesulfonamide; or pharmaceutically acceptable salts thereof.

4. The compound of claim 1 selected from the group consisting of N-[[(4-chlorophenyl)amino]-carbonyl]cyclopentanesulfonamide; N-[[(4-chlorophenyl)amino]carbonyl]phenylthiomethanesulfonamide; or pharmaceutically acceptable salts thereof.

5. The compound of claim 1 which is N-[[(4-chlorophenyl)amino]carbonyl]cyclopentanesulfonamide and the salts thereof.

6. The compound of claim 1 which is N-[[(4-chlorophenyl)amino]carbonyl]phenylthiomethanesulfonamide and the salts thereof.

7. A pharmaceutical formulation comprising a compound of claim 1 in combination with a pharmaceutically acceptable excipient.

8. The formulation of claim 7 wherein said compound is selected from the group consisting of N-[[3-chloro-4-fluorophenyl)amino]carbonyl]-2-propanesulfonamide; N-[[(3,4-dichlorophenyl)amino]carbonyl]-2-propanesulfonamide; N-[[(3-trifluoromethyl-4-chlorophenyl)amino]carbonyl]-2-propanesulfonamide; N-[[(4-chlorophenyl)amino]carbonyl]cyclohexanesulfonamide; N-[[(4-bromophenyl)amino]carbonyl]cyclopentanesulfonamide; N-[[(4-chlorophenyl)amino]carbonyl]-2-ethoxyethanesulfonamide; N-[[(3,4-dichlorophenyl)amino]carbonyl]-2-butanesulfonamide; N-[[((4-fluorophenyl)amino]carbonyl]cyclopentanesulfonamide; N-[[(4-chlorophenyl)amino]carbonyl]cyclopentanesulfonamide; N-[[(4-chlorophenyl)amino]carbonyl]phenylthiomethanesulfonamide; or pharmaceutically acceptable salts thereof.

9. A compound of claim 3 which is N-[[(4-chlorophenyl)amino]carbonyl]cyclopentanesulfonamide.

* * * * *